Figures 1, 2:
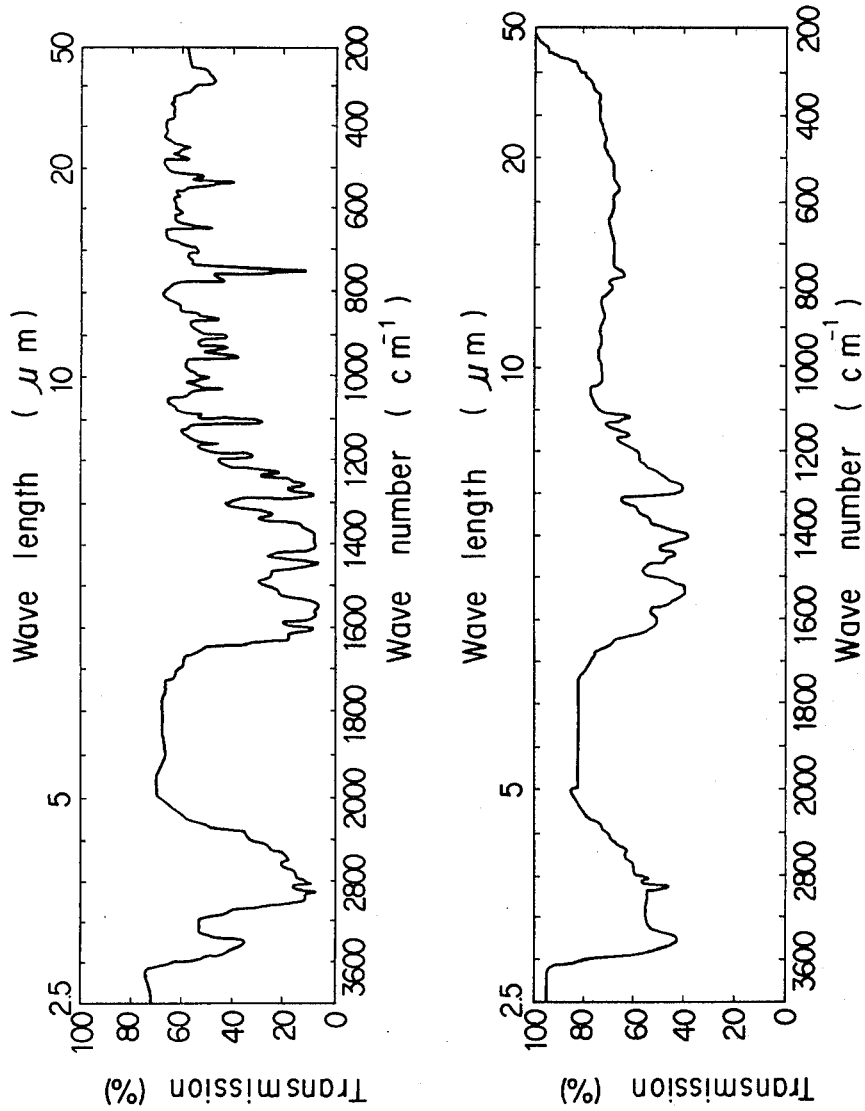

United States Patent [19]

Takita et al.

[11] Patent Number: 4,464,396

[45] Date of Patent: Aug. 7, 1984

[54] 4-[N-(HYDROXYBENZYL)AMINOMETHYL]-CYCLOHEXANE-1-CARBOXYLIC ACID

[75] Inventors: Hitoshi Takita; Yutaka Mukaida; Sakuo Noda; Hidetoshi Kobayashi, all of Tokyo, Japan

[73] Assignee: Kureha Kagaku Kogyo Kabushiki Kaisha, Tokyo, Japan

[21] Appl. No.: 440,616

[22] Filed: Nov. 10, 1982

[30] Foreign Application Priority Data

Nov. 20, 1981 [JP] Japan ................. 56-186691

[51] Int. Cl.³ .................. C07C 101/30; A61K 31/195
[52] U.S. Cl. ..................... 424/319; 562/451; 560/42; 260/501.15; 260/501.17; 424/316
[58] Field of Search ............... 562/424, 442, 451; 424/319, 316; 260/501.17, 501.15; 560/42

[56] References Cited

U.S. PATENT DOCUMENTS 4,163,060 7/1979 Tartog et al. ............. 562/444
4,396,627 8/1983 Ainswath et al. ........... 562/451

FOREIGN PATENT DOCUMENTS 57-59848 4/1982 Japan .................. 562/444

Primary Examiner—James H. Reamer
Attorney, Agent, or Firm—Oblon, Fisher, Spivak, McClelland & Maier

[57] ABSTRACT

A novel compound of 4-[N-(hydroxybenzyl)aminomethyl]-cyclohexane-1-carboxylic acid represented by the general formula (I):

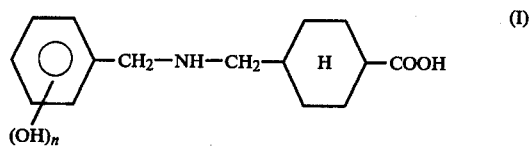

wherein n is an integer of 1 to 3, or a salt or an ester thereof which has specific pharmacological activities, a method for preparing the derivative and a pharmacological composition in dosage unit form comprising the derivative as an active ingredient are disclosed herein.

16 Claims, 2 Drawing Figures

4-[N-(HYDROXYBENZYL)AMINOMETHYL]CYCLOHEXANE-1-CARBOXYLIC ACID

This invention relates to 4-[N-(hydroxybenzyl)aminomethyl]cyclohexane-1-carboxylic acids or salts or esters thereof, to their production and to pharmacological compositions containing them.

The present invention provides a 4-[N-(hydroxybenzyl)aminomethyl]cyclohexane-1-carboxylic acid (hereinafter referred to as the present compound) represented by the general formula (I):

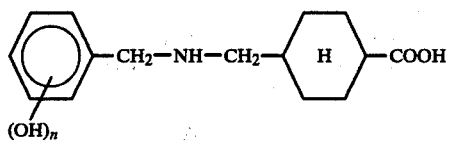

(I)

wherein n is an integer from 1 to 3, or a salt or an ester thereof. In the general formula (I), the cyclohexane ring may be in either the trans- or the cis form, or a mixture thereof. And the present invention includes various compounds regarding the number and the position of the hydroxy group since in the general formula (I) there are five possible positions for hydroxy group, 2-, 3-, 4-, 5-, and 6-position of the benzene nucleus, and n denotes an integer of 1, 2 or 3.

As the present compounds, for example, the following compounds are exemplified:

4-[N-(2'-hydroxybenzyl)aminomethyl]cyclohexane-1-carboxylic acid,
4-[N-(3'-hydroxybenzyl)aminomethyl]cyclohexane-1-carboxylic acid,
4-[N-(4'-hydroxybenzyl)aminomethyl]cyclohexane-1-carboxylic acid,
4-[N-(2',3'-dihydroxybenzyl)aminomethyl]cyclohexane-1-carboxylic acid,
4-[N-(2',4'-dihydroxybenzyl)aminomethyl]cyclohexane-1-carboxylic acid,
4-[N-(3',4'-dihydroxybenzyl)aminomethyl]cyclohexane-1-carboxylic acid,
4-[N-(2',3',4'-trihydroxybenzyl)aminomethyl]cyclohexane-1-carboxylic acid.

The salts of the present compound include alkali or alkaline earth metal salts such as the sodium salt, potassium salt, calcium salt or magnesium salt, ammonium salts or primary-, secondary, tertiaty- and quanternary ammonium salts. The esters are preferably lower alkyl esters in which the alkyl group has 1 to 3 carbon atoms, such as methyl-, ethyl- or n- or isopropyl.

The present compounds and their salts and esters are preferably prepared by the process described below, although it may be prepared by the other methods. Preferably, therefore, compounds of the general formula (I) and esters thereof are prepared by reacting a hydroxybenzaldehyde derivative represented by the general formula (II):

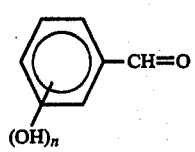

(II)

wherein n is as defined above, with 4-aminomethylcyclohexane-1-carboxylic acid which has the formula (III):

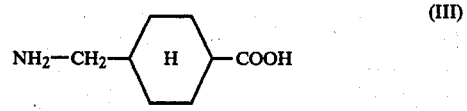

(III)

wherein the cyclohexane ring can be in either the trans- or cis form or a mixture thereof, or an ester, preferably a lower alkyl ester, thereof to obtain a derivative of 4-[N-(hydroxybenzylidene)aminomethyl]cyclohexane-1-carboxylic acid represented by the formula (IV):

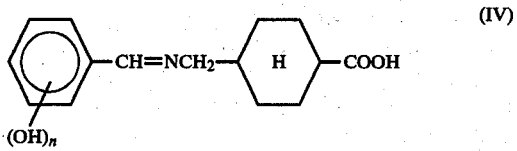

(IV)

wherein n is as defined above, and then reducing the thus obtained derivative (IV). The reaction between the compound of the formula (II) and the compound of the formula (III) is preferably carried out in an organic solvent at room temperature or under heating. Any organic solvent may be used for the reaction provided it may not participate in the reaction. For example, a lower alcohol such as methanol or ethanol, benzene, toluene, dioxane or tetrahydrofuran is conventionally used for the reaction. The reduction of the derivative (IV) is preferably carried out in an organic solvent, for example, a lower alcohol such as methanol or ethanol and acetic acid in the presence of a reducing agent such as sodium borohydride or an aminoboron compound, for instance dimethylaminoborohydride.

The present compound can be isolated by treating the reaction mixture in a known manner such as extraction, recrystallization and the like after the reaction has been completed.

A salt of the present compound can be prepared by the conventional method involving neutralization by using a base such as a hydroxide, carbonate or bicarbonate of an alkali or alkaline earth metal, for example sodium, potassium, calcium or magnesium, or of ammonium or a primary-, secondary- or tertiary amine. For example, a sodium salt can be obtained by neutralizing a present compound (an acid form) with an aqueous solution of sodium hydroxide under an atmosphere of an inert gas at a temperature lower than 100° C., usually at from 0° to 50° C.

An ester of the present compound can be also prepared by the conventional method involving esterification.

The present compound and salts and esters thereof show the pharmacological activities such as an inhibitory effect on polynuclear leukocyte migration, anti-inflammatory activity, anti-rheumatic activity, anti-allergic activity and the like and a low acute toxicity, as will be shown in Example. Accordingly, the present compound is useful in therapy for the treatment of chronic diseases such as asthma, rheumatism, inflammation or systemic lupus erythematosus (SLE). The present invention therefore also provides a pharmaceutical composition comprising the present compound or a pharmaceutically acceptable salt or ester thereof as active ingredient, together with a pharmaceutically acceptable carrier and/or adjuvant.

The composition of the present invention can be administered perorally, rectally or by injection in the various dosage forms. Two or more of the present compound and their pharmaceutically acceptable salts or esters may be used. Other pharmaceutically active materials may be incorporated in the pharmaceutical composition.

The dosage form of the composition may be as a tablet, sublingual tablet, powder, capsule, troche, aqueous or oily solution, suspension, emulsion, syrup or aqueous or oily injection. Examples of the carrier include water, gelatin, lactose, starch, pectin, magnesium stearate, stearic acid, talc, vegerable oil, gum arabic, polyalkylene glycol, vaseline, sorbitan tri-oleate, polyoxyethylene-sorbitan mono-oleate, alkylphenol, aliphatic alcohols and polyvinyl pyrrolidone. In the composition, if necessary, an edulcorant, flavour, tintorial agent, a conventional pharmaceutical adjuvant, may be used.

The content of the present compound or pharmaceutically acceptable salt or ester thereof in a pharmaceutical composition of the present invention may be suitably varied, for example, within a range of 0.01 to 100% by weight of the composition, preferably 0.05 to 80% by weight of the composition.

The pharmaceutical composition of the present invention can be administered to a human or animal parenterally, for example, rectally, by injection (hypodermic, intramuscular or intravenous, or drip) or preferably perorally (for example sublingually). A dose of the pharmaceutical composition of the invention can consist of 0.1 to 500 mg, preferably 0.5 to 200 mg per day per kilogram of body weight in the case of peroral administration to a human, and 0.01 to 200 mg, preferably 0.1 to 100 mg in the case of parenteral administration. The pharmaceutical composition can be administered one to four times a day. However the dose of the pharmaceutical composition depends on for example age, the individual being treated and the condition of a disease. Doses outside the above-mentioned range may be used.

The followings are the more detailed explanation of the present invention while referring to examples, however, it should be understood that the scope of the present invention is never restricted to Examples shown as follows.

EXAMPLE 1

Preparation of trans-4-[N-(2'-hydroxybenzyl)aminomethyl]cyclohexane-1-carboxylic acid 8.0 g (30.6 mmol) of trans-4-[N-(2'-hydroxybenzylidene)aminomethyl]cyclohexane-1-carboxylic acid obtained by condensation of 2-hydroxybenzaldehyde with trans-4-aminomethylcyclohexane-1-carboxylic acid was dissolved in 100 ml of acetic acid. Into the resulting solution, a solution of 0.829 mg of sodium borohydride in 25 ml of isopropylamine was added dropwise at a room temperature while stirring. This mixed solution was reacted at room temperature for 2 hours. After the reaction was over, the solvent was evaporated off from the reaction mixture under a reduced pressure at 60° C., and the residue was dissolved in 400 ml of distilled water. The colorless powdery crystals that were salted out by adding sodium chloride into the solution were filtered and vacuum-dried. 4.98 g of trans-4-[N-(2'-hydroxybenzyl)aminomethyl]cyclohexane-1-carboxylic acid was obtained in a yield of 60.9%.

The characteristics of the compound thus obtained were as follows.

(1) Melting point; 233° to 234° C. with decomposition, (2) Elementary analysis:

|  | C(%) | H(%) | N(%) |
|---|---|---|---|
| theoretical: | 68.42 | 8.04 | 5.32 |
| experimental: | 68.15 | 8.10 | 5.30 |

(3) Infrared absorption (IR) spectrum by KBr method, as shown in FIG. 1 of the accompanying drawings.

EXAMPLE 2

Preparation of trans-4-[N-(3',4'-dihydroxybenzyl)aminomethyl]cyclohexane-1-carboxylic acid 5.0 g (18.0 mmol) of trans-4-[N-(3',4'-dihydroxybenzylidene)aminomethyl]cyclohexane-1-carboxylic acid obtained by condensation of 3,4-dihydroxybenzaldehyde with trans-4-aminomethylcyclohexane-1-carboxylic acid was dissolved in 50 ml of methanol. Into the resulting solution, 0.963 mg (25.4 mmol) of sodium borohydride was added while stirring at room temperature, and after further adding 30 ml of methanol, the mixture was reacted for 10 minutes at room temperature. After the reaction was over, a minute amount of insoluble matters were removed by filtration followed by neutralizing the reaction mixture with hydrochloric acid, the solvent was evaporated off from the reaction mixture under a reduced pressure to obtain 4.03 g of a crude product. The crude product was dissolved in a mixture of 8 ml of distilled water and 21 ml of concentrated hydrochloric acid at 60° to 65° C. After leaving the solution at 0° to 5° C., the colorless prismatic crystals were collected by filtration and dried to obtain 3.20 g of hydrochloride of trans-4-[N-dihydroxybenzyl)aminomethyl]cyclohexane-1-carboxylic acid.

By de-hydrochlorination of the hydrochloride while using an ion-exchanging resin column (AMBERLITE®IR-45), 2.43 g of a crystalline product was obtained.

The characteristics of the compound thus obtained were as follows.

(1) Melting point; 209° to 212° C. with decomposition, (2) Elementary analysis;

|  | C(%) | H(%) | N(%) | O(%) |
|---|---|---|---|---|
| theoretical: | 60.59 | 7.80 | 4.71 | 26.91 |
| experimental: | 60.4 | 7.8 | 4.9 | — |

(3) IR spectrum; as shown in FIG. 2 of the accompanying drawings, (4) Nuclear magnetic resonance (NMR) spectrum in dimethylsulphoxide; $\delta = 0.79-1.91(9H, m)$, $1.96-2.16(1H)$, $2.45-2.53(1H)$, $3.61(2H, s)$, $6.62(2H, s)$, $6.74(1H, s)$.

(5) Mass spectrum; $M^+ = 279$

According to the above-mentioned data and the result of differential thermobalance determination, it was confirmed that the thus produced compound was monohydrate of the titled compound.

EXAMPLE 3

Examination of pharmacological activity and acute toxicity

The pharmacological activity and acute toxicity of the present compounds and their salts and esters were examined. The specimens examined are as follows:

Specimen

I; Trans-4-[N-(2'-hydroxybenzyl)aminomethyl]cyclohexane-1-carboxylic acid obtained in Example 1,
II; Trans-4-[N-(3',4'-dihydroxybenzyl)aminomethyl]cyclohexane-1-carboxylic acid obtained in Example 2.

Comparative Specimen

III; indomethacin having an anti-inflammatory activity and being commercially available.

The examination was carried out according to the methods described below:

(1) Examination for inhibitory effect on polynuclear leukocyte migration:

Rat's polynuclear leukocyte migration was examined by the Boyden method.

(2) Examination for acute toxicity:

Acute toxicity was examined by administering perorally an aqueous solution of each Specimen to female JCL-ICR mice 5 to 6 weeks after their birth.

The results are shown in the Table.

TABLE

| Specimen | Concentration of 50% inhibition of polynuclear leukocyte migration IC$_{50}$($\mu$M) | Acute toxicity LD$_{50}$ (mg/Kg) |
|---|---|---|
| I | 340 | >3000 |
| II | 32 | >3000 |
| III | 240 | 30 |

As shown in the Table, the present compounds have been found to show very specific pharmacological activity and a low acute toxicity. Accordingly the present compound can be used in a pharmaceutical composition which is safe and can be employed in preventing various diseases.

What is claimed is:

1. 4-[N-(hydroxybenzyl)aminomethyl]cyclohexane-1-carboxylic acid represented by the general formula (I):

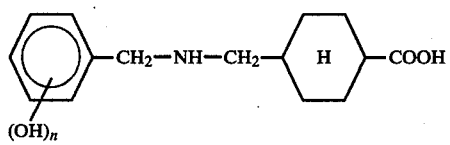

wherein n is an integer of 1 to 3, or a salt or an ester thereof.

2. The compound of claim 1, which is trans-4-[N-(2'-hydroxybenzyl)aminomethyl]cyclohexane-1-carboxylic acid or a salt or an ester thereof.

3. The compound of claim 1, which is trans-4-[N-(3',4'-dihydroxybenzyl)aminomethyl]cyclohexane-1-carboxylic acid or a salt or an ester thereof.

4. A pharmaceutical composition in dosage unit form comprising 4-[N-(hydroxybenzyl)aminomethyl]cyclohexane-1-carboxylic acid represented by the general formula (I):

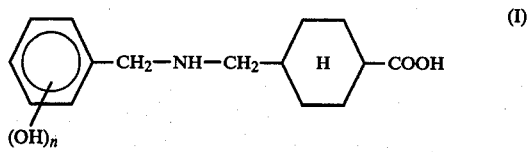

wherein n is an integer of 1 to 3, or a salt or an ester thereof.

5. The composition of claim 4 wherein the dosage form is selected from the group consisting of a tablet, powder, capsule, troche, aqueous or oily solution, suspension, emulsion, syrup and aqueous or oily injection.

6. The composition of claim 4, comprising 0.01 to 500 mg of the compound.

7. The composition of claim 6, comprising 0.5 to 200 mg of the compound.

8. The compound of claim 1, having the formula: 4-[N-(2'-hydroxybenzyl)aminomethyl]cyclohexane-1-carboxylic acid.

9. The compound of claim 1, having the formula: 4-[N-(3'-hydroxybenzyl)aminomethyl]cyclohexane-1-carboxylic acid.

10. The compound of claim 1, having the formula: 4-[N-(4'-hydroxybenzyl)aminomethyl]cyclohexane-1-carboxylic acid.

11. The compound of claim 1, having the formula: 4-[N-(2',3'-dihydroxybenzyl)aminomethyl]cyclohexane-1-carboxylic acid.

12. The compound of claim 1, having the formula: 4-[N-(2',4'-dihydroxybenzyl)aminomethyl]cyclohexane-1-carboxylic acid.

13. The compound of claim 1, having the formula: 4-[N-(3',4'-dihydroxybenzyl)aminomethyl]cyclohexane-1-carboxylic acid.

14. The compound of claim 1, having the formula: 4-[N-(2',3',4'-trihydroxybenzyl)aminomethyl]cyclohexane-1-carboxylic acid.

15. The compound of claim 1, in the form of a salt, wherein the cation is selected from the group consisting of sodium, potassium, calcium, magnesium, NH$_4$ and primary, secondary, tertiary or quaternary ammonium.

16. The compound of claim 1 in the form of an ester selected from the group consisting of methyl ester, ethyl ester, and n- or isopropyl esters.

* * * * *